United States Patent
Nadershahi et al.

(10) Patent No.: US 9,402,537 B2
(45) Date of Patent: Aug. 2, 2016

(54) MINIMALLY OBSTRUCTIVE COMPACT SPECULUM

(71) Applicant: Alfred E. Mann Institute for Biomedical Engineering at the University of Southern California, Los Angeles, CA (US)

(72) Inventors: Afshin Nadershahi, Northridge, CA (US); Sudeep Deshpande, Newbury Park, CA (US)

(73) Assignee: ALFRED E. MANN INSTITUTE FOR BIOMEDICAL ENGINEERING AT THE UNIVERSITY OF SOUTHERN CALIFORNIA, Los Angeles, CA (US)

(*) Notice: Subject to any disclaimer, the term of this patent is extended or adjusted under 35 U.S.C. 154(b) by 0 days.

(21) Appl. No.: 14/894,113

(22) PCT Filed: Aug. 3, 2015

(86) PCT No.: PCT/US2015/043414
§ 371 (c)(1),
(2) Date: Nov. 25, 2015

(87) PCT Pub. No.: WO2016/022470
PCT Pub. Date: Feb. 11, 2016

(65) Prior Publication Data
US 2016/0183778 A1 Jun. 30, 2016

Related U.S. Application Data

(60) Provisional application No. 62/032,590, filed on Aug. 3, 2014.

(51) Int. Cl.
*A61B 1/32* (2006.01)
*A61B 1/303* (2006.01)
*A61B 1/31* (2006.01)

(52) U.S. Cl.
CPC . *A61B 1/32* (2013.01); *A61B 1/303* (2013.01); *A61B 1/31* (2013.01)

(58) Field of Classification Search
CPC ............. A61B 1/303; A61B 1/32; A61B 1/31
See application file for complete search history.

(56) References Cited

U.S. PATENT DOCUMENTS 643,221 A    2/1900   Chapman
5,722,936 A  3/1998   Trulio
(Continued)

FOREIGN PATENT DOCUMENTS

WO    90/03813 A1    4/1990

OTHER PUBLICATIONS

ISA/US. International Search Report and Written Opinion of the International Searching Authority, dated Oct. 29, 2015, for PCT Application PCT/US15/43414, entitled "Minimally Obstructive Compact Speculum" (PCT Application of which instant application is a submission to the United States under 35 U.S.C. 371).

*Primary Examiner* — Ellen C Hammond
(74) *Attorney, Agent, or Firm* — McDermott Will & Emery LLP

(57) ABSTRACT

Medical instruments, particularly structurally-adjustable speculums and retractors for obstetrical and gynecological operations, procedures, and examinations, including a minimally obstructive compact speculum or retractor. The compact speculum may comprise a first wing and a second wing; and a hinge comprising at least one hinge component. The compact speculum may further comprise a ratchet that releasably holds the wings in an open position. The hinge component may comprise the ratchet, an illumination source, a fluid handler, a light guide, a lubrication source, or a combination thereof. The compact speculum may be a vaginal speculum.

16 Claims, 6 Drawing Sheets

(56) References Cited

U.S. PATENT DOCUMENTS

| | | |
|---|---|---|
| 2004/0059190 A1 | 3/2004 | Matlock |
| 2012/0083658 A1* | 4/2012 | Hahn ........................ A61B 1/32 600/205 |
| 2013/0041229 A2 | 2/2013 | Hahn et al. |
| 2014/0364695 A1* | 12/2014 | Nadershahi ............ A61B 17/42 600/205 |
| 2014/0364698 A1* | 12/2014 | Nadershahi .............. A61B 1/32 600/215 |

* cited by examiner

MINIMALLY OBSTRUCTIVE COMPACT SPECULUM

CROSS-REFERENCE TO RELATED APPLICATION

This application is a national phase of International Application No. PCT/US2015/043414, filed on 3 Aug. 2015, entitled "Minimally Obstructive Compact Speculum," which is based upon and claims priority to U.S. provisional patent application 62/032,590, entitled "Minimally Obstructive Compact Speculum," filed Aug. 3, 2014. The entire content of both of these applications is incorporated herein by reference.

TECHNICAL FIELD

This disclosure relates generally to medical instruments, particularly to structurally-adjustable speculums and retractors for obstetrical and gynecological operations, procedures, and examinations. This disclosure relates more particularly to a minimally obstructive compact speculum or retractor.

DESCRIPTION OF RELATED ART

Devices that have been proposed for obstetrical and gynecological operations, procedures, and examinations may not be entirely satisfactory for a variety of reasons. They may obstruct the vision of the deep internal parts of the vaginal cavity that they are intended to expose. They may also constrain the movement of the physicians' hands, obstruct or limit the range of motion of instruments, and reduce the open work area for the surgeon. They may also fail to prevent tissue and/or fluids from obscuring inspection and obstructing the work area for the surgeon. This can reduce the efficiency and effectiveness of examinations and procedures.

A vaginal speculum (or retractor) is a medical instrument that allows a healthcare provider to visualize the interior of the vagina, as well as distal portion of the uterus and the cervix. Most speculums comprise two blades assembled together and held by a handle. The blades and the handle form an approximately 90-degree angle. As the user holds the handle, a lever attached to the top blade allows it to open away from the inferior blade.

When the instrument is inserted into the vagina, the blades are separated in order to keep the anterior and posterior walls apart. In that position, the cervix and the walls of the vagina can be seen, so long as the patient does not have excess loose vaginal tissue. Since no part of the speculum is in direct contact with the lateral walls of the vagina, the clinician tends to open the blades wider than necessary in order to keep the lateral walls apart and conduct an adequate examination. This excessive distension of the vaginal tissue can be a source of discomfort to the patient. Commonly-used speculums are generally made of metal, such as stainless steel, and are designed to be sterilized between examinations. Disposable speculums are being used more and more frequently, particularly for convenience and decreased risk of transfer of contamination from one patient to another.

Two types of patients tend to have excessive vaginal tissue: those who are multiparous and those who are obese. The multiparous patient often will have a relaxation of the levator ani musculature, which results in a tendency for the vaginal walls to collapse toward the midline during speculum examination. These muscles may be overstretched from the cumulative weight of numerous pregnancies, as well as the mechanical stress of multiple vaginal deliveries.

Patients who are obese may also present this internal vaginal anatomy as a result of an increase in the amount of loose connective tissue beneath the pelvic peritoneum. When these patients have a vaginal speculum examination, the loose lateral vaginal walls similarly collapse toward the midline as the blades attempt to maintain the anterior and posterior walls apart. This collapse prevents a complete and possibly crucial visualization of the cervix for the purpose of cervical cultures, pap smears, ruptured membranes, visual assessment of a degree of dilation, and biopsy.

This problem has been addressed by the combined use of two instruments, one conventional speculum and a lateral retractor having two blades facing normal to those of the speculum. Such usage is suggested, for example, by literature provided by CooperSurgical, Inc. (product catalog, 1997).

This problem also has been addressed by encasing the blades of a conventional speculum within a condom having its distal end removed.

Waters (U.S. Pat. No. 4,994,070) discloses a vaginal speculum that comprises a sheet member that is rolled into an elongate shape and is expandable to form a hollow tube. When expanded, the tube retains the vaginal walls away from the midline in all directions. The entire content of this patent is incorporated herein by reference.

Hayes (U.S. Pat. No. 4,492,220) discloses a vaginal speculum that has disposable covers for the blades to prevent cross-contamination of patients examined with the same instrument. The entire content of this patent is incorporated herein by reference.

Francois (U.S. Pat. No. 6,432,048) discloses a vaginal speculum that has a flexible membrane structure, such as a pair of membranes that extend between the blades, adapted to retain the lateral walls of the vagina in spaced relation from a midline of the vagina when the blades are in the open position. The entire content of this patent is incorporated herein by reference.

Thus, conventional speculums may fail to provide a sufficient open work area for the healthcare practitioner to visualize and access the cervix and the vaginal walls of the patient. In some patients, a conventional speculum may obstruct and interfere with visualization of the desired work area by the healthcare practitioner. Modified speculums or alternative designs for bivalve speculums, while possibly aiding in retaining the lateral walls of the vagina, may compromise visualization of and access to the vaginal walls.

SUMMARY

This disclosure relates generally to medical instruments, particularly to structurally-adjustable speculums and retractors for obstetrical and gynecological operations, procedures, and examinations. This disclosure particularly relates to a minimally obstructive compact speculum or retractor.

In one example, the compact speculum may comprise a first wing and a second wing; and a hinge. The hinge may form a housing. The hinge may be attached to the first and the second wings, permitting the wings to rotate about the hinge when moving from a closed to an open position.

In this disclosure, the speculum, the wings, and the hinge each may have a proximal end, a distal end, an exterior surface, and an interior surface. In this disclosure, the hinge may have an axis of rotation.

In this disclosure, the wings and the hinge may form a canopy that, when the wings are in the open position, creates and only partially surrounds an interior space that is not surrounded by any other portion of the compact speculum.

In this disclosure, no portion of the compact speculum obstructs any portion of a length of the interior space opposite the hinge between the proximal end and the distal end of the compact speculum when the wings are in the open position.

In one example, the hinge may comprise at least one hinge component. The hinge may form a housing. The housing may house the at least one hinge component. For example, the at least one hinge component may substantially be within the housing. The at least one hinge component may comprises a ratchet, an illumination system, a light guide, a fluid handler, a lubrication system. For example, the ratchet may substantially be within the housing. The illumination system may substantially be within the housing. The light guide may substantially be within the housing. The fluid handler may substantially be within the housing. The lubrication system may substantially be within the housing.

Examples of this compact speculum are: the at least one hinge component may comprise a ratchet, the at least one hinge component comprises an illumination system, the at least one hinge component further comprises a light guide, the at least one hinge component comprises a fluid handler; and the at least one hinge component comprises a lubrication system. In example, the at least one hinge component may comprise a ratchet and an illumination system. In another example, the at least one hinge component may comprise a ratchet and an illumination system and a fluid handler.

In another example, the compact speculum may further comprise a ratchet that releasably holds the wings in an open position. The hinge may house the ratchet. The ratchet may comprise a first ratchet component and a second ratchet component. The first ratchet component may rotate together with the first wing. The second ratchet component may rotate together with the second wing. The first ratchet component may be attached to the first wing. The second ratchet component may linearly move along the hinge's axis of rotation to engage with or disengage from the first ratchet component, thereby releasably holding the wings in an open position.

In one example, the compact speculum may further comprise a ratchet release button that, when pressed, releases the ratchet. In another example, the hinge may comprise a ratchet release button. The button may protrude from the proximal end of the hinge. The ratchet may further comprise a ratchet engagement spring that releasably engages the first ratchet component with the second ratchet component. The ratchet release button may be attached to the second ratchet component.

The compact speculum may further comprise a key and a keyway. The keyway may be longer than the key. The key may engage with the keyway to attach the second ratchet component to the second wing in a way that locks rotation of the second ratchet component to the rotation of the second wing while allowing the linear motion of the second ratchet component.

In one example, the hinge may comprise a pin and at least two hinge cylinders. In this example, each hinge cylinder may be attached to one of the wings.

In another example, the hinge may comprise a pin and one hinge cylinder. In this example, the hinge cylinder may be attached to one of the wings.

The pin may be hollow and may house the hinge component. At least one hinge cylinder may pivot around the pin. The ratchet may comprise a first ratchet component and a second ratchet component. The first ratchet component may rotate together with the first wing and the second ratchet component may rotate together with the second wing. The first ratchet component may be attached to the first wing. The second ratchet component may be attached to the pin. The second ratchet component and the pin may together linearly move along the hinge's axis of rotation to engage with or disengage from the first ratchet component.

The pin may comprise a key. The at least one hinge cylinder may comprise a keyway. At least one hinge cylinder that pivots around the pin may be attached to the second wing. The keyway may be longer than the key. The key may engage with the keyway to attach the pin and the second ratchet component to the second wing so as to lock rotation of the pin and the second ratchet component to the rotation of the second wing while allowing the linear motion of the pin and the second ratchet component.

The illumination system may be automatically turned by movement of the wings away from each other. The illumination system may be automatically turned off by movement of the wings towards each other. The hinge may house the illumination system and the illumination system may be manually turned on and/or turned off. The illumination system may comprise a pull-tab. The illumination system may be manually turned on by pulling the pull-tab. The illumination system may comprise a manual switch. The illumination system may be manually turned on by manipulating the manual switch. The illumination system may comprise a light-emitting diode.

The fluid handler may be configured to remove fluid from and/or deliver fluid to tissue in the vicinity of the speculum. The fluid handler may comprise a conduit. The conduit may comprise a perforated segment. The conduit may comprise a tube with a perforated distal end. The conduit may comprise a tube leading to a perforated plate. The speculum may further comprise a docking port. The fluid handler and the speculum may be attachable to each other via the docking port.

The lubrication system may comprise a reservoir that can store a lubricant and a lubricant delivery channel that delivers lubricant stored in the reservoir to an outer surface of the speculum.

The wings may comprise serrated wing edges.

Each wing may comprise a lip at its proximal end. The proximal end of each wing may flare outward to form a thumb paddle.

The compact speculum may further comprise thinned portions, protrusions, or a combination thereof, on the exterior surface of the hinge, the wings, or both the hinge and the wings.

The compact speculum may be transparent.

The canopy may substantially block fluid flow through the exterior surface of the canopy.

The compact speculum may be a vaginal speculum.

This disclosure further relates to a method. For example, the method may comprise a method for a medical intervention. For example, the method may comprise a method for a medical intervention to a vagina. The method for a medical intervention may comprise inserting the compact speculum into a body opening. In this exemplary method, the hinge component may further comprise a fluid handler. The method may further comprise removing fluids from the body opening using the fluid handler, after inserting the speculum. In another example, the method may further comprise applying a vacuum to the fluid handler.

In one exemplary method, the hinge component may further comprise an illumination system. The method may further comprise turning on the illumination system.

The hinge component may further comprise a fluid handler. The fluid handler may be movable with respect to the hinge. The method may further comprise re-positioning the fluid handler within the body opening after inserting the speculum.

The method may further comprise repositioning the speculum after inserting the speculum by rotating the speculum within the body opening. The method may further comprise repositioning the speculum after inserting the speculum by removing the speculum from the body opening, and then re-inserting speculum within the body opening.

The method may further comprise spreading the two wings apart while in the body opening. The method may further comprise closing the wings after spreading the wings apart and then removing the speculum from the body opening.

Any combination of features of the speculums and methods of their use that are described herein may also be made and followed.

These, as well as other components, steps, features, objects, benefits, and advantages, will now become clear from a review of the following detailed description of illustrative embodiments, the accompanying drawings, and the claims.

BRIEF DESCRIPTION OF DRAWINGS

The drawings disclose illustrative embodiments. They do not set forth all embodiments. Other embodiments may be used in addition or instead. Details which may be apparent or unnecessary may be omitted to save space or for more effective illustration. Conversely, some embodiments may be practiced without all of the details which are disclosed. When the same numeral appears in different drawings, it refers to the same or like components or steps.

The following reference numerals and letters are used in the drawings: 100 speculum, 103 fluid handler, 104 fluid port, 110 right wing, 111 right wing hinge cylinder, 112 right thumb paddle, 120 right serrated edges, 210 left wing, 211 left wing hinge cylinder, 212 left thumb paddle, 214 hole, 215 keyway, 220 left serrated edges, 300 LED, 301 batteries, 302 illumination system spring, 303 distal ratchet wheel, 304 proximal ratchet wheel, 305 ratchet engagement spring, 306 pull-tab, 307 ratchet gear teeth, 308 ratchet release button, 400 pin, 401 key, 500 hinge, 600 illumination system, x lateral axis, y vertical axis, and z longitudinal axis.

DETAILED DESCRIPTION OF ILLUSTRATIVE EMBODIMENTS

Figure 1:
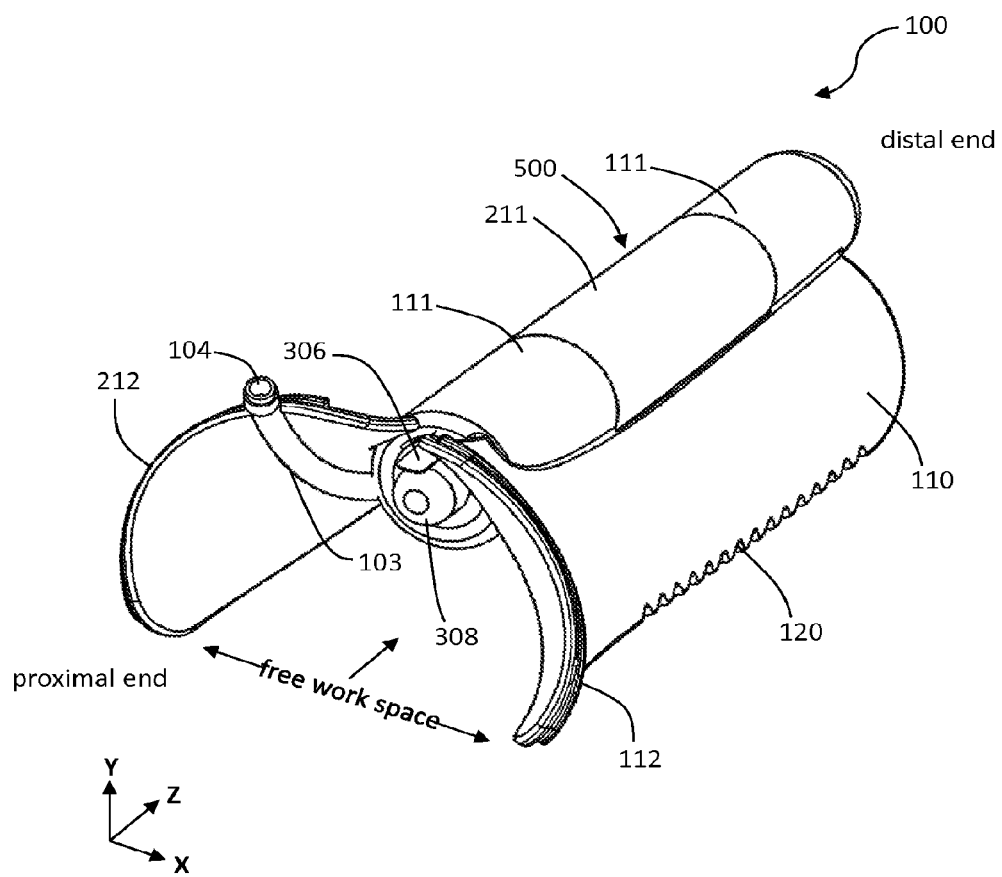
FIG. 1 shows an isometric view of an exemplary compact speculum, wherein the two wings are in an open position.

Illustrative embodiments are now discussed. Other embodiments may be used in addition or instead. Details which may be apparent or unnecessary may be omitted to save space or for a more effective presentation. Conversely, some embodiments may be practiced without all of the details which are disclosed.

The components, steps, features, objects, benefits and advantages which have been discussed are merely illustrative. None of them, nor the discussions relating to them, are intended to limit the scope of protection in any way. Numerous other embodiments are also contemplated. These include embodiments which have fewer, additional, and/or different components, steps, features, objects, benefits and advantages. These also include embodiments in which the components and/or steps are arranged and/or ordered differently.

This disclosure relates generally to medical instruments, particularly to structurally-adjustable speculums and retractors for obstetrical and gynecological operations, procedures, and examinations. This disclosure relates particularly relates a minimally obstructive compact speculum or retractor.

This disclosure relates to Nadershahi et al. "Minimally obstructive retractor" U.S. Pat. No. 9,050,048; Nadershahi et al. "Speculum for Obstetrical and Gynecological Exams and Related Procedures" U.S. Patent Application Publication No. 2014/0364695; and Nadershahi et al. "Minimally Obstructive Retractor For Vaginal Repairs" U.S. Patent Application Publication No. 2014/0364698. The entire content of each of these publications are incorporated herein by reference.

An example of a minimally obstructive compact speculum or retractor ("compact speculum", "speculum", or "device") may comprise: two wings (a first wing and a second wing), and a hinge, as shown in FIGS. 1-6. The hinge may comprise a hinge component. The hinge may be affixed to the first and the second wings. The wings may be rotatable about the hinge when moving from a closed to an open position.

The compact speculum may further comprise a ratchet. In one example, the ratchet may releasably hold the wings in an open position. In another example, the ratchet may releasably lock the wings in an open position. The hinge component may comprise the ratchet, an illumination system, a light guide, a fluid handler, a lubrication system, or a combination thereof. For example, the hinge component may comprise the ratchet. For example, the hinge component may further comprise an illumination system, a light guide, a fluid handler, a lubrication system, or a combination thereof.

The hinge may form a housing. The housing may house the hinge component. The housing may house the ratchet, the illumination system, the light guide, the fluid handler, the lubrication system, or a combination thereof. For example, the housing may house the ratchet. In another example, the housing may further house the illumination system. Yet, in another example, the housing may further house the illumination system and the fluid handler.

The speculum, the wings, and the hinge may each have a proximal end, a distal end, an exterior surface, and an interior surface. The wings and the hinge may form a canopy that may create and only partially surround an interior space that is not surrounded by any other portion of the compact speculum when the wings are in the open position. Any portion of a length of the interior space opposite the hinge between the proximal end and the distal end, when the wings are in the open position, is hereafter called "free work space", as shown in FIG. 1. The free work space may be free of the compact speculum's portions (or components). That is, in this example, the compact speculum's portions may not obstruct the free work space. The free work space may be substantially free of the compact speculum's portions (or components). That is, in this example, the compact speculum's portions may not substantially obstruct the free work space.

An example of a compact speculum may comprise two wings attached by a hinge, the wings being rotatable about the hinge when moving from a closed to an open position. The hinge and the wings may provide a continuous canopy to prevent fluids and/or loose tissue from obscuring inspection and obstructing the work area for the healthcare provider. The hinge may house a ratchet system that functions to retain various user-selected angles of retraction. Furthermore, the hinge may house an illumination system, such as a battery-powered light-emitting diode (LED), to illuminate the cervix, vaginal walls, and surrounding structures. Furthermore, the hinge may house a fluid (e.g. smoke and/or liquid) evacuation channel, and/or a light guide that functions to redirect and/or disperse the light.

The hinge may provide a single axis of rotation, which may be a function similar to those used in devices and mechanisms such as door hinges and other uniaxial devices. Types of hinges that may be employed in various examples of the speculum include barrel hinges, continuous/piano hinges, concealed hinges, gear hinges, or pivot hinges. The exemplary hinges illustrated in FIGS. 1-6 may commonly be referred to as barrel hinges or continuous hinges.

Figure 2:
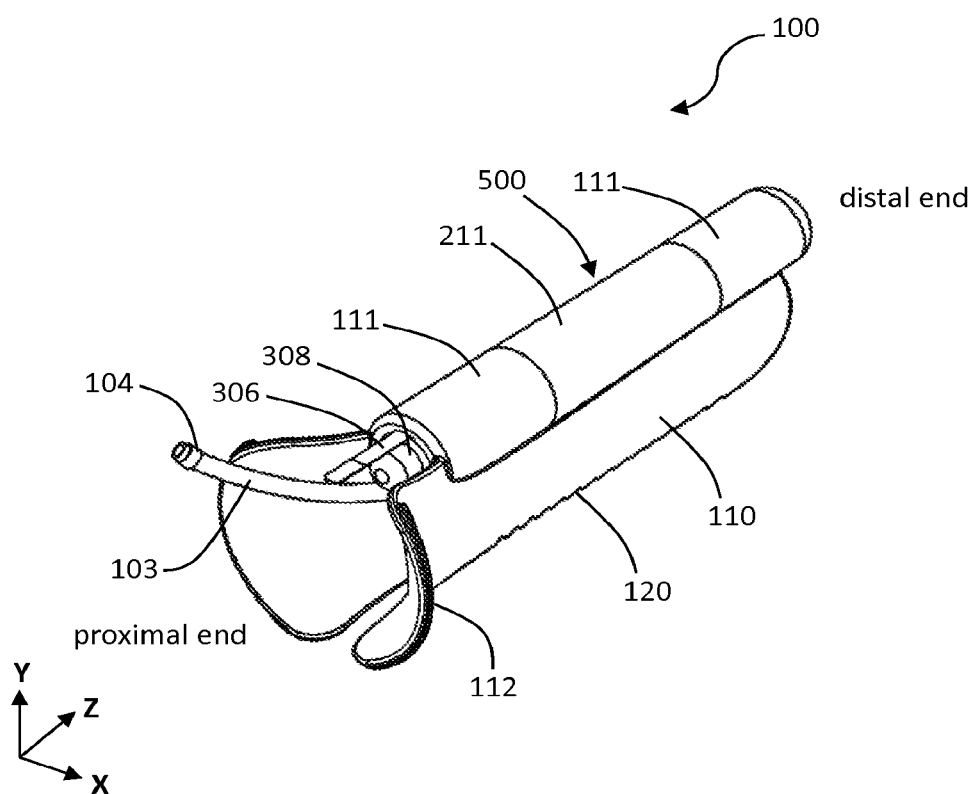
FIG. 2 shows an isometric view of an exemplary compact speculum, wherein the two wings are in a closed position.

The exemplary speculums of this disclosure may have a proximal end and a distal end, wherein the proximal end is manipulated by the healthcare provider, and the distal end is the aspect of the device inserted first into the patient. After the speculum is inserted in a vagina, the proximal end is nearer the vaginal introitus, and the distal end is nearer the uterine cervix. The proximal end and the distal end of the compact speculum are shown in FIGS. 1-2.

The axis of rotation about the hinge (the hinge axis) is herein referred to as the device's longitudinal axis, "z". The axis spanning from wing to wing (and that in most exemplary embodiments is perpendicular or approximately perpendicular to the device's longitudinal axis) is herein referred to as the device's lateral axis, "x". The axis passing through the hinge and the space between the wings (and that in most exemplary embodiments is perpendicular or approximately perpendicular to the device's longitudinal and lateral axes) is herein referred to as the device's vertical axis, "y". These axes, x, y, and z are shown in FIGS. 1-6. The speculum may be described as having a left side and a right side, in reference to the hinge being in the topmost position when viewing the proximal end of the speculum.

Accordingly, various parts of exemplary speculums may be described as having proximal and distal aspects along the longitudinal axis, z. For instance, each wing may be described as having a proximal end and a distal end, wherein the proximal end of a wing is closer to the proximal end of the speculum, and the distal end of a wing is closer to the distal end of the speculum. Accordingly, various parts of exemplary speculums may be described as having top and bottom aspects, along the vertical axis, y. For clarity and convenience, these reference positions may be used throughout this disclosure.

Using the terminology described above, the device's longitudinal axis extends from the proximal end of the speculum to the distal end of the speculum. After the speculum is inserted in a vagina, the device's longitudinal axis is directed from the vaginal introitus (proximally) to the vaginal fornices (distally).

The wings and the hinge may together form a canopy. This canopy may only partially surround an interior space that is not surrounded by any other portion of the speculum when the wings are in the open position (spread apart from each other).

In one example, the compact speculum may be a speculum suitable for a body opening. The body opening may be any body opening. Examples of a body opening may be a vagina, a rectum, a surgical incision, and an oral cavity. For example, the compact speculum may be a vaginal speculum.

In one example, the canopy may be formed such that the fluid flow through the exterior surface of the canopy, defined by the exterior surfaces of the wings and hinge, is substantially blocked. For example, the fit between the parts of the hinge may be tight enough to substantially block the flow of fluid. Thus, when the speculum is inserted into a vagina and opened such that its wings are spread apart, the canopy comprising the hinge and wings spans several vaginal walls (for instance, the anterior and both lateral vaginal walls), while leaving the cervix, introitus, and the remaining vaginal wall (in the described instance, the posterior vaginal wall), exposed for visualization and access by the healthcare provider. The speculum may be rotated and/or repositioned to provide the user with, alternately, access to different aspects of the vagina. For instance, the user may first position the speculum with its hinge against the anterior vaginal wall, exposing the posterior vaginal wall; then rotate the speculum 180 degrees about the axis of its hinge, so its hinge is against the posterior vaginal wall, the speculum thereby exposing the anterior vaginal wall. Thus, the hinge and wings form a canopy that affords an open work area and enhances visualization to users about a vaginal wall of a patient when the device is within a vagina and especially when the speculum is in the open position.

FIGS. 1-6 depict various views of an exemplary minimally obstructive speculum (100). The exemplary speculum (100) may comprise a right wing (110) and a left wing (210) affixed to a hinge (500). These wings may be solid. These wings may also be hollow and shell-like to provide a convex exterior and, conversely, a generally concave interior to permit visual as well as manual access thereto. The wings may be of a shape, contour, thickness, angle, radius, and size to hold up the vaginal walls during various procedures.

The top aspect of the wings (110, 210) may comprise complementary parts of the hinge (500). For example, the top aspect of each wing may form a section of the hinge. Thus, the hinge may comprise a right wing hinge cylinder (111) and a left wing hinge cylinder (211). Alternatively, the top aspect of the wings may form opposing gears of a gear hinge. The hinge (500) may permit the wings (110, 210) to flex or pivot about the hinge (500) to permit visual and manual access to the interior of a body passage.

The hinge (500) may comprise a hollow cylinder ("hinge cylinder"). This hinge may further comprise a pin (400) housed within the hollow cylinder, such that the hinge cylinder is configured to pivot around the pin. In other words, the pin may provide the pivot for the swiveling action of the hinge. The pin (400) may further comprise a hollow cylinder ("tube"). This tube may house a ratchet, an illumination system, a light guide, a fluid handler, a lubrication system, or a combination thereof. Alternatively, the hinge (500) itself may house a ratchet, an illumination system, a light guide, a fluid handler, a lubrication system, or a combination thereof. The hinge (500) may further comprise a ratchet release button (308) configured to allow the user to release a ratchet mechanism and/or turn an illumination system on and/or off. This button may protrude from the proximal end of the hinge (500) to it is easily accessible to the user.

Each hinge cylinder may be affixed to one of the wings.

The exemplary speculum (100) may comprise a ratchet mechanism. This ratchet mechanism may serve to provide structural support to the wings (110, 210) to counteract the force of the vaginal walls on the wings (110, 210). In other words, the ratchet mechanism may be configured to prevent the wings (110, 210) from moving toward each other under the force of the vaginal walls. The ratchet mechanism may serve to hold the wings (110, 210) in various positions with respect to each other. That is, the ratchet mechanism may lock the wings (110, 210) to prevent them from moving toward each other when in an open position such as during retraction, whereas the user may desire to have the wings (110, 210) closer to each other during insertion and removal of the speculum (100). Various wing positions may also be desired for different body shapes, sizes, or morphologies. After the speculum is inserted into a vagina, the vaginal walls may be separated by manually spreading the wings (110, 210) apart, at which point a ratchet mechanism may hold the device in its "open" configuration. The wings (110, 210) may later be brought together (and the speculum thereby "closed") by actuating the ratchet release button (308) or other mechanism to release the ratchet. This button may be located in the front of the hinge and accessible by the user's fingers. In one example, the speculum's wings (110, 210) can maintain discrete retraction positions by means of a mechanical ratchet mechanism.

The ratchet may comprise a first ratchet component and a second ratchet component. The first ratchet component may be configured to rotate together with the first wing, and the second ratchet component may be configured to rotate together with the second wing. The first ratchet component may be affixed to the first wing. The second ratchet component may linearly move along the hinge's axis of rotation to engage or disengage from the first ratchet component, thereby releasably holding the wings in an open position.

The compact speculum may further comprise a ratchet release button that, when pressed, releases the ratchet. The hinge may comprise a ratchet release button. The ratchet release button may protrude from the proximal end of the hinge. The ratchet release button may be affixed to the second ratchet component. The ratchet may further comprise a ratchet engagement spring that releasably engages the first ratchet component with the second ratchet component.

The compact speculum may further comprise a key and a keyway that is longer than the key. The key may be configured to engage with the keyway to affix the second ratchet component to the second wing in a way that locks rotation of the second ratchet component to the rotation of the second wing while allowing the liner motion of the second ratchet component.

In one example, the key and keyway mechanism may be between the hinge cylinder and the pin. In this example, at least one hinge cylinder pivots around the pin and is attached to the second wing. Each hinge cylinder may be affixed to one of the wings. The pin may be hollow and house the hinge component. The ratchet may comprise a first ratchet component and a second ratchet component. The first ratchet component may be configured to rotate together with the first wing, and the second ratchet component may be configured to rotate together with the second wing. The first ratchet component may be affixed to the first wing. The second ratchet component may be attached to the pin. The second ratchet component and the pin may be configured so they can together linearly move along the hinge's axis of rotation to engage or disengage from the first ratchet component. The pin may comprise a key. At least one of the hinge cylinders that is attached to the second wing and pivots around the pin may comprise a keyway. The keyway may be longer than the key. The key may engage with the keyway to affix the pin and the second ratchet component to the second wing so as to lock rotation of the pin and the second ratchet component to the rotation of the second wing while allowing the linear motion of the pin and the second ratchet component.

The ratchet may comprise a proximal ratchet wheel (304) and a distal ratchet wheel (303), representing the ratchet components mentioned above, wherein the proximal ratchet wheel (304) is configured to rotate with one of the wings and the distal ratchet wheel (303) is configured to rotate with the other wing. These ratchet wheels (303, 304) may be designed to reversibly engage each other by having interlocking teeth. These interlocking teeth may be ramped or biased in one direction to allow the engaged ratchet wheels (303, 304) to rotate against each other in one direction (corresponding to opening the speculum), but to lock and prevent rotation against each other in the other direction (corresponding to closing the speculum). The ratchet may further comprise a spring mechanism, wherein a ratchet engagement spring (305) is configured to releasably engage the distal ratchet wheel (303) with the proximal ratchet wheel (304), preventing rotation of the ratchet wheels (303, 304) relative to each other in one direction but not the other, thereby preventing these parts from pivoting relative to each other about the hinge (500) in that direction, and preventing the wings (110, 210) from being brought together to close the speculum (100). The speculum (100) may further comprise a ratchet release button (308), wherein the ratchet release button is configured to release the ratchet by separating the distal and proximal ratchet wheels (303, 304).

In one example, the proximal ratchet wheel (304) is assembled permanently into the proximal end of the right wing hinge cylinder (111) such that rotational motion of the right wing hinge cylinder (111) translates directly to the same motion of the proximal ratchet wheel (304). The distal ratchet wheel (303) may be assembled permanently into the proximal end of pin (400) such that rotational motion of the left wing hinge cylinder (211) translates directly to the same motion of the distal ratchet wheel (303). The pin (400) may comprise a key (401) that interacts with a keyway (215) in the left wing (210) such that any rotational motion of the left wing (210) would translate to the pin (400) while allowing the pin (400) to move along the longitudinal axis within the hollow cavities of the hinge cylinders (111, 211). This movement along the longitudinal axis would involve the distal and proximal ratchet wheels (303, 304) to engage and disengage with each other, their engagement being maintained by a ratchet engagement spring (305), and their disengagement being actuated by the user pressing a ratchet release button (308). A ratchet engagement spring (302) may push the distal ratchet wheel (303) toward the proximal ratchet wheel (304) to engage their ratchet gear teeth (307), thereby locking the ratchet in at least one radial direction. The ratchet release button (308) may be a proximal extension of the center of the distal ratchet wheel that protrudes through the hollow center of the proximal ratchet wheel and out of the proximal end of the hinge, exposed to the user. Pushing the push-button pushes the distal ratchet wheel against the ratchet engagement spring (302) and away from the proximal ratchet wheel, thereby disengaging the ratchet wheels' teeth and temporarily releasing the ratchet mechanism from the locked position, allowing the user to reposition the speculum's wings (110, 210) as desired. Once the ratchet release button (308) is released, the ratchet engagement spring pushes the distal ratchet wheel toward the proximal ratchet wheel, re-engaging the ratchet wheels' teeth and thereby locking the ratchet wheels and the wings (110, 211) in position. The proximal ratchet wheel (304) may also function to hold or seal other components, such as an LED (300), batteries (301), light guide, and/or spring(s), inside the pin (400). The distal ratchet wheel (304) may be integrated with the ratchet release button (308) and the distal end of the pin (400) such that it forms a single unit. The pin (400) may comprise a key (401) that assembles with a keyway (215) in the left wing hinge cylinder (211), forming a keyed joint. The keyed joint allows transfer of rotational motion from the left wing (210) to the pin (400), ratchet release button (308), and distal ratchet wheel (303) in the same direction and opposite to the right wing (110).

Thus, when the wings are opened, the proximal ratchet wheel (304) rotates along with one wing, in the same direction; while the distal ratchet wheel (303) rotates with the other wing, in the other direction. Depressing the ratchet release button (308) disengages the ratchet gear teeth (307) on the distal ratchet wheel (303), thereby allowing the wings (110, 210) to open and/or close. Upon releasing the ratchet release button (308) the ratchet engagement spring re-engages the ratchet gear teeth (307) and locks the wings in place.

The compact speculum may also comprise an on-off system for the illumination system to make the illumination system user-controlled or automatic.

In one example, the illumination system may comprise an LED (300) that may be powered by one or more batteries (301). An LED system spring (302) may provide pressure contact between the LED and the batteries to ensure electrical continuity. The illumination system may be housed by the pin (400) and/or the hinge (500). The LED (300), batteries (301) and/or the LED system spring (302) may be assembled into the pin (400) and/or the hinge (500).

The illumination system may manually be turned on and/or turned off. In one example, the illumination system may comprise a pull-tab (306), wherein the illumination system is manually turned on by pulling the pull-tab (306). In the initial off state of the LED, the pull-tab (306) may be placed between the battery surfaces may interrupt the normal electrical path between the batteries, thereby maintaining the off state. Pulling out the pull-tab from between the batteries allows contact between the batteries and resumes electricity from the batteries to the LED to turn the light on. The pull-tab may be a thin strip of plastic sheet. The pull-tab may be accessible from the exterior of the speculum at the proximal end of the hinge (500). Part of the pull-tab (306) may be exposed at the proximal end of the hinge (500). Once the pull-tab (306) is removed completely, it may permanently turn the illumination system on. In another example, the illumination system may comprise a manual switch, wherein the illumination system is manually turned on by activating the manual switch. This manual switch could be shared by the ratchet system, providing both functions of turning the light on and/or off, and releasing the ratchet.

The illumination system may automatically be turned on in conjunction with movement of the wings (110, 210) away from each other, and/or automatically turned off in conjunction with movement of the wings (110, 210) towards each other. In one example, an optical sensor switch may be used to activate the light function. The switch may be placed within the hinge (500) or between the hinge (500) and the wings (110, 210), such that the sensor of the switch is occluded from ambient light when the speculum (100) is open, or alternatively when it is closed. In another example, a mechanical switch may be placed between the wings (110, 210) where the mechanical switch may by pressed in the off position when the wings (110, 210) are closest together (with the speculum in the "closed" position), thus keeping the light function off. When the wings (110, 210) are moved away from each other, this may release the switch, thereby turning the switch to the on position, completing the electrical circuit and turning the light function on. In another example, a mechanical push button switch may be placed within the hinge (500) such that when the wings (110, 210) are moved away from each other, this may flip the switch, thereby turning the switch to the on position, completing the electrical circuit and turning the light on. In another example, a breakoff plastic feature may be used to trigger a switch (or an incomplete circuit by a separated wire connection) to turn on the light. In the closed position, one of the wings may be connected to the switch via a plastic feature or tab. When the wings (110, 210) are pulled away from each other, this plastic tab could break, consequently activating the switch (or completing the connection between the separated wire) to turn on the light. With this mechanism, the device light function could stay on until the batteries are drained of their power. A variation of this mechanism may use the plastic tab as a cover over the optical sensor switch. On pulling the wings (110, 210) away from each other, the plastic tab could break and expose the optical sensor, thereby completing the electrical circuit and turning the light on.

The illumination system may comprise a light-emitting diode ("LED") (300). In some examples, the speculum (100) may comprise a plurality of LEDs located at various portions of hinge (500) and/or the wings (110, 210).

In some examples, a single compression spring may simultaneously serve the following two functions: pressing the batteries (301) of an illumination system against each other; and pushing a distal ratchet wheel (303) toward a proximal ratchet wheel (304) to engage their ratchet gear teeth (307), thereby locking the ratchet in at least one radial direction.

In some examples, the speculum may comprise a light-guide. This light guide may be made of clear plastic. In some examples, an LED (300), batteries (301), spring(s) and/or pull-tab (306) may be external to the pin (400), with a light-guide incorporated into the pin (400) to redirect, focus, and/or disperse the light. In some examples, the light-guide may be made of the same material as, and possibly be formed from an outcropping of, the hinge (500), pin (400), and/or wings (110, 210) of the speculum (100).

In some embodiments, a light guide may also function as a fluid handler by comprising a tube, a fluid channel (103), and/or a fluid port (104).

The speculum (100) may further comprise a fluid handler configured to remove fluid and/or smoke from and/or deliver fluid to tissue in the vicinity of the speculum (100) during use.

The fluid handler may comprise holes (214) for inflow and/or outflow of fluid and/or smoke. In some examples, the fluid handler may comprise a conduit. The conduit may comprise a perforated segment, a non-perforated segment, or a combination thereof. The conduit may comprise a tube, which may have a perforated distal end. The conduit may comprise a tube leading to a perforated plate.

The fluid handler may comprise a tube, a fluid channel (103), and/or a fluid port (104) that may be attached to an external vacuum aspirator device for various procedures. The fluid handler may be integrated within the hinge (500), it may be located alongside the hinge (500), or it may be integrated or attached to a wing.

The fluid handler may be integrated into and/or onto the hinge (500) the pin (400), and/or one or both of the wings (110, 210). The fluid handler may be movable with respect to the hinge.

The speculum may further comprise a docking port, wherein the fluid handler comprises a temporarily attachable fluid handler, and wherein the fluid handler and the speculum are attachable to each other via the docking port.

The hinge (500) may comprise a hole (214). The right wing (110) may comprise a hole (214). The left wing (210) may comprise a hole (214). The left wing hinge section (211) may comprise a hole (214). The right wing hinge section (111) may comprise a hole (214). Both the left wing hinge section (211) and the right wing hinge section (111) may comprise a plurality of holes (214). The pin (400) may comprise a hole (214).

Figure 5:
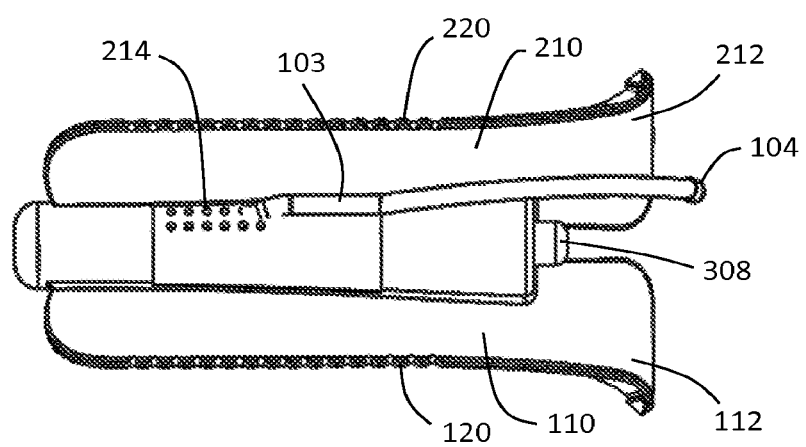
FIG. 5 shows a bottom view of an exemplary compact speculum.
Figure 5:
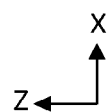
Figure 6:
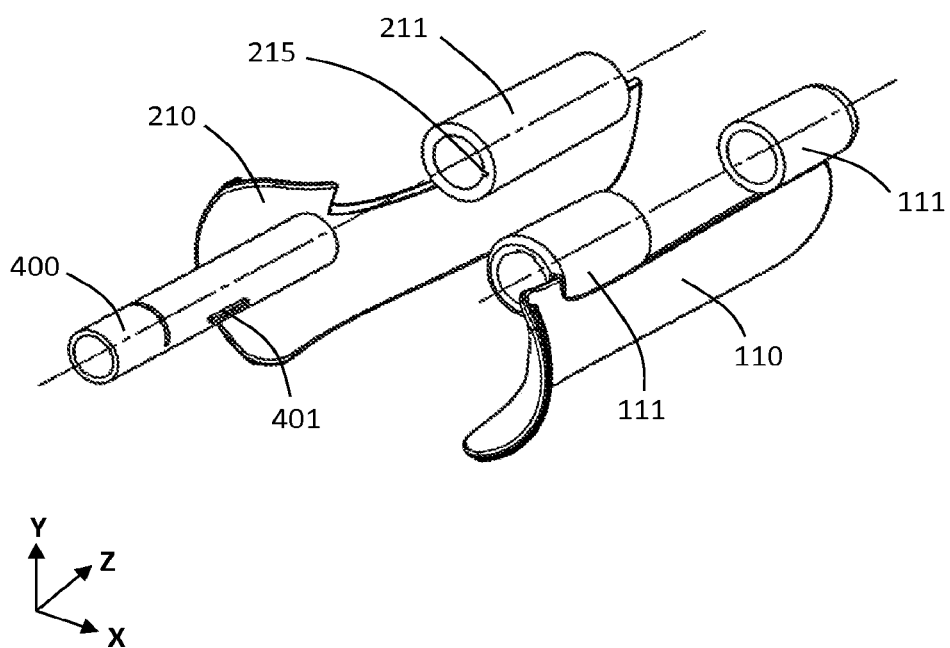
FIG. 6 shows an exploded view of an exemplary compact speculum.

In one exemplary speculum (100), the outer surface of the speculum (100), which may be in contact with the tissue, may not have a hole (214). That is, for example, when the speculum (100) is placed in the vagina for medical treatment purposes, the hole (214) may be configured to be only on the inner surface of the speculum (100) as shown in FIG. 5.

In some examples, the speculum (100) may comprise a lubrication system. This lubrication system may comprise a lubricant-containing reservoir integrated with the body of the speculum (100), and a lubrication channel for delivering the biocompatible lubricant. For example, the reservoir may be located on, or integrated within, the pin (400), and/or the wings (110, 210). A lubrication channel may provide lubrication to an outer surface of the speculum (100).

Each wing (110, 210) may further comprise a lip at its proximal end. This lip, consisting of a protuberance or flaring of the proximal end of the wing, may increase stability of the speculum (100), helping to secure its position with respect to the vagina, and/or help to prevent the speculum from penetrating too deeply into the vagina.

The proximal end of each wing (110, 210) may flare outward to form a thumb paddle. These right and left thumb paddles (112, 212), at the proximal end of the speculum (100), may be used to grasp the speculum during insertion, to spread the wings apart ("opening the speculum"), to reposition the speculum, to position the wings closer together, to close the speculum, and/or to remove the speculum. The thumb paddles may comprise raised surfaces or texture to provide enhanced grip. The thumb paddles may also help to prevent the speculum from penetrating too deeply into the vagina. The thumb paddles may also increase stability of the speculum, and help to secure its position with respect to the vagina.

The hinge (500), the wings (110, 210), or both the hinge and the wings may also comprise protruded and/or thinned portions to provide friction and prevent the speculum (100) from undesirable movement during use. These thinned portions are thinner than the remaining portions of the hinge and/or wing. The protruded and/or thinned portions may protrude from the hinge and/or wings or be etched or carved into the hinge and/or wings. The protruded and/or thinned portions may be anywhere on the hinge and/or wings. The protruded and/or thinned portions may comprise various shapes or forms such as grooves, serrations, cross-hatches, bumps, or other morphologies to provide adequate friction with the tissue, while not damaging the tissue or causing discomfort to the patient. In other examples, the exterior contact surfaces of the speculum may comprise grooves, blunted barbs, or other textures to provide friction and to resist slippage of the device within the vaginal cavity. In one example, the wings comprise serrated wing edges (120, 220). The right serrated edges (120) and left serrated edges (220) may be at the edges of the wings (110, 210) farthest from the hinge (500). The serrated edges (120, 220) may prevent undesired movements, such as slippage, of the speculum (100) when it is in the vagina.

Figure 3:
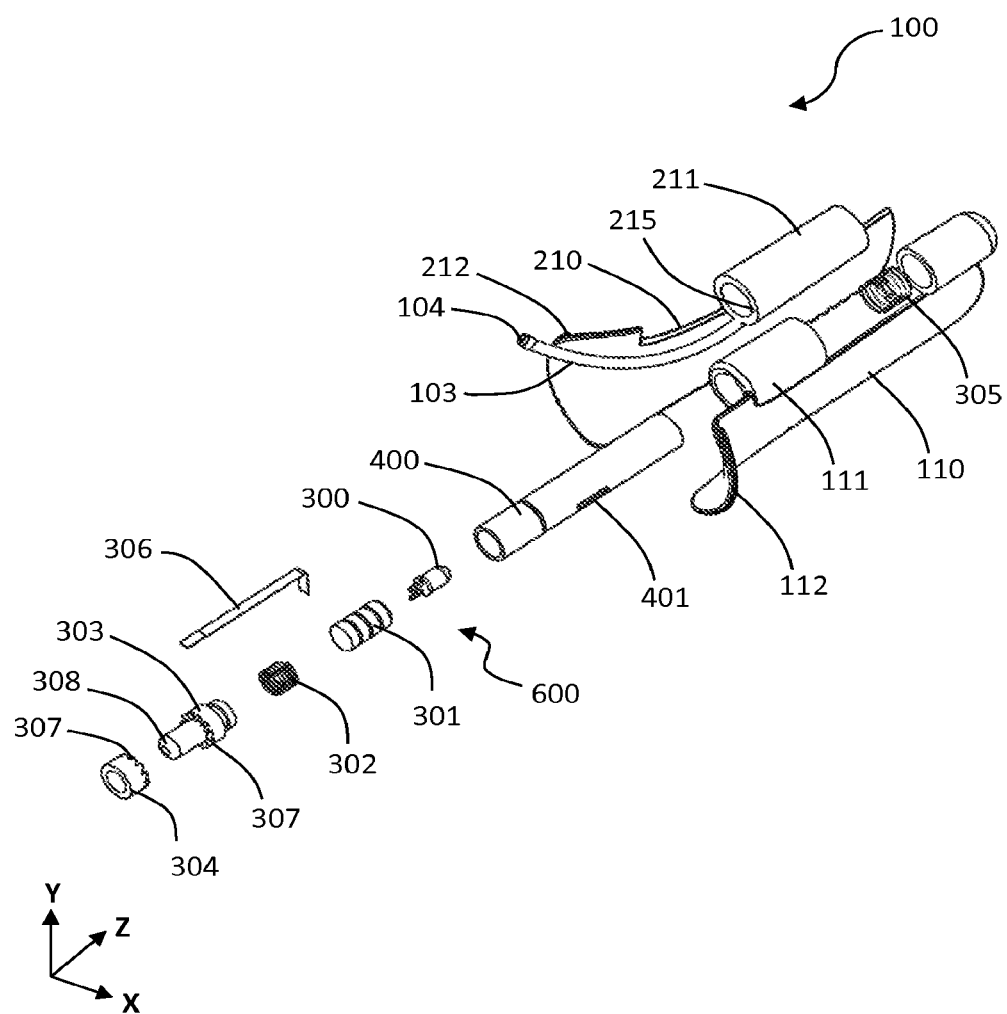
FIG. 3 shows an exploded view of an exemplary compact speculum.
Figure 4:
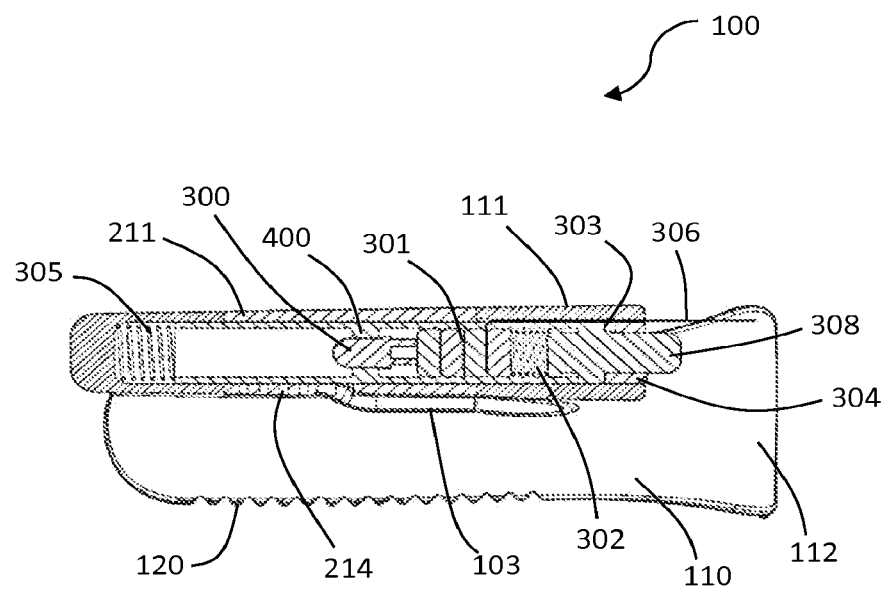
FIG. 4 shows a cross-sectional view of an exemplary compact speculum.

The following description of an assembly process refers to the exemplary speculum shown in FIG. 3 and provides further information on structures and features of exemplary devices. A ratchet engagement spring (305) may comprise a compression spring that may be placed into the hollow cavity of the distal end of the right wing hinge cylinder (111). The left wing hinge cylinder (211) may then be placed in-line with the right wing hinge cylinder (111). The pin (400) housing the LED (300), batteries (301), illumination system spring (302), and distal ratchet wheel (303) may be inserted through the hollow cavity of the pin (400) and then placed through the hinge cylinders (111, 211) to complete the hinge assembly. The relative rotational motion between the wings may be translated through the pin (400) by means of a keyed joint between the pin (400) and the hinge cylinder (211). The pin (400) may consist of a key (401) that interacts with a keyway (215) in the left wing (210) such that any rotational motion of the left wing (210) would translate to the pin (400) yet allow the pin (400) relative axial movement within the hollow cavities of the left wing hinge cylinder (211). That is, when the wings (110, 210) are opened outward, the pin (400) may rotate along with the left wing (210) in the same rotational direction, and rotating in the opposite rotational direction with respect to the right wing (110). This relative rotational motion and interaction between the ratchet wheels (303, 304) provides the discrete wing positions, while the depression of the ratchet release button (308) provides the temporary disengagement between the ratchet wheels (303, 304) that provides the user the ability to open/close the wings (110, 210) to the desired position. Other examples may follow the description above, but with left and right sides switched.

This speculum (100) may be simple and inexpensive to manufacture, use, and maintain. The speculum may be for single (one-time) use, fully or partially disposable. Alternatively, the speculum may be for repeated or multiple uses.

The speculum (100) may be sterilizable by ethylene oxide, gamma radiation or other process known to those skilled in the art. It may be disposable or reprocessable. Also, the device may be made of different sizes and/or thicknesses to accommodate different ages and sizes of patients. The device may be coated with a material to facilitate inspection and movement. For example, a lubricant can be used to coat the device to facilitate insertion and retrieval.

The speculum may be transparent, opaque, non-transparent, or a combination thereof. The speculum (100) may be made out of clear, rigid, biocompatible plastic, to provide maximum clarity during procedures. In addition, a clear plastic may provide maximum illumination from the LED light, thereby providing improved visualization of the vaginal walls and surrounding tissue during procedures. The clear plastic may function to reflect or diffuse the light from the LED. The wings (110, 210) may be made of clear, rigid, biocompatible plastic, or may be made of biocompatible metals typically used to create surgical instruments. The hinge cylinders (111, 211) may be made of clear, rigid, biocompatible plastic. The ratchet release button (308) and the ratchet gear (304) may be made of clear or opaque, rigid, biocompatible plastic or may be made of biocompatible metal. The pin (400) may be made of clear, rigid, biocompatible plastic.

In some examples, the speculum may comprise a polymer such as acrylonitrile butadiene styrene (ABS), polyurethane, acetal plastics, or another material known to those skilled in the art that provides both structural rigidity and flexibility. It may comprise flexible plastic material such as polyamide sold under the trade name "NYLON," polytetrafluoroethylene sold under the trademark "TEFLON". Alternatively, a polypropylene plastic or a high density polyethylene plastic may be used to manufacture the speculum. The device may be made of a transparent plastic in order to enhance the viewing area. It may also be made of metal. Mixtures or composites of these materials may also be used to manufacture the minimally obstructive speculum.

A method for a vaginal medical intervention may comprise inserting the speculum into a vagina. The method may further comprise removing fluids from the vagina using the fluid handler, after inserting the speculum. The method may further comprise turning on the illumination system, or having it turn on automatically. The method may further comprise applying a vacuum to the fluid handler. If the fluid handler is movable with respect to the hinge, the user may re-position the fluid handler within the vagina after inserting the speculum. The method may further comprise repositioning the speculum after inserting the speculum by rotating the speculum within the vagina. This may involve slightly or fully closing the speculum, and possibly reopening it. The user may also reposition the speculum by removing it from the vagina then re-inserting speculum into the vagina in a different position or orientation. The method may further comprise spreading the speculum's wings apart while the speculum in the vagina. The method may later comprise closing the wings and then removing the speculum from the vagina. The device may be fully disposable.

Any combination of above products, methods of production of such products, and methods of application of such products is within the scope of the instant disclosure.

In this disclosure, the indefinite article "a" and phrases "one or more" and "at least one" are synonymous and mean "at least one".

The components, steps, features, objects, benefits, and advantages that have been discussed are merely illustrative. None of them, nor the discussions relating to them, are intended to limit the scope of protection in any way. Numerous other embodiments are also contemplated. These include embodiments that have fewer, additional, and/or different components, steps, features, objects, benefits, and/or advantages. These also include embodiments in which the components and/or steps are arranged and/or ordered differently.

The previous description of embodiments is provided to enable any person skilled in the art to make or use the retractors and speculums. Various modifications to these embodiments will be readily apparent to those skilled in the art, and the generic principles defined herein may be applied to other embodiments without departing from the spirit or scope of the retractors and speculums. Thus, the retractors and speculums are not intended to be limited to the embodiments shown herein but are to be accorded the widest scope consistent with the principles and novel features disclosed herein.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

All articles, patents, patent applications, and other publications that have been cited in this disclosure are incorporated herein by reference.

The phrase "means for" when used in a claim is intended to and should be interpreted to embrace the corresponding structures and materials that have been described and their equivalents. Similarly, the phrase "step for" when used in a claim is intended to and should be interpreted to embrace the corresponding acts that have been described and their equivalents. The absence of these phrases from a claim means that the claim is not intended to and should not be interpreted to be limited to these corresponding structures, materials, or acts, or to their equivalents.

The scope of protection is limited solely by the claims that now follow. That scope is intended and should be interpreted to be as broad as is consistent with the ordinary meaning of the language that is used in the claims when interpreted in light of this specification and the prosecution history that follows, except where specific meanings have been set forth, and to encompass all structural and functional equivalents.

Relational terms such as "first" and "second" and the like may be used solely to distinguish one entity or action from another, without necessarily requiring or implying any actual relationship or order between them. The terms "comprises," "comprising," and any other variation thereof when used in connection with a list of elements in the specification or claims are intended to indicate that the list is not exclusive and that other elements may be included. Similarly, an element preceded by an "a" or an "an" does not, without further constraints, preclude the existence of additional elements of the identical type.

None of the claims are intended to embrace subject matter that fails to satisfy the requirement of Sections 101, 102, or 103 of the Patent Act, nor should they be interpreted in such a way. Any unintended coverage of such subject matter is hereby disclaimed. Except as just stated in this paragraph, nothing that has been stated or illustrated is intended or should be interpreted to cause a dedication of any component, step, feature, object, benefit, advantage, or equivalent to the public, regardless of whether it is or is not recited in the claims.

The abstract is provided to help the reader quickly ascertain the nature of the technical disclosure. It is submitted with the understanding that it will not be used to interpret or limit the scope or meaning of the claims. In addition, various features in the foregoing detailed description are grouped together in various embodiments to streamline the disclosure. This method of disclosure should not be interpreted as requiring claimed embodiments to require more features than are expressly recited in each claim. Rather, as the following claims reflect, inventive subject matter lies in less than all features of a single disclosed embodiment. Thus, the following claims are hereby incorporated into the detailed description, with each claim standing on its own as separately claimed subject matter.

The invention claimed is:

1. A compact speculum comprising:
a first wing and a second wing;
a hinge that forms a housing and that is attached to the first and the second wings, permitting the wings to rotate about the hinge when moving from a closed to an open position; and
a ratchet substantially within the housing that releasably holds the wings in the open position;
wherein the speculum, the wings, and the hinge each has a proximal end, a distal end, an exterior surface, and an interior surface;
wherein the wings and the hinge form a canopy that, when the wings are in the open position, creates and only partially surrounds an interior space that is not surrounded by any other portion of the compact speculum,
wherein the ratchet comprises a first ratchet component and a second ratchet component; and wherein the first ratchet component rotates together with the first wing, and the second ratchet component rotates together with the second wing,
wherein the first ratchet component is attached to the first wing,
wherein no portion of the compact speculum obstructs any portion of a length of the interior space opposite the hinge between the proximal end and the distal end of the compact speculum when the wings are in the open position, and
wherein the second ratchet component moves linearly along the hinge's axis of rotation to engage with or disengage from the first ratchet component, thereby releasably holding the wings in an open position.

2. The compact speculum of claim 1 further comprising a key and a keyway; wherein the keyway is longer than the key; and wherein the key engages with the keyway to attach the second ratchet component to the second wing in a way that locks rotation of the second ratchet component to the rotation of the second wing while allowing the linear motion of the second ratchet component.

3. A compact speculum comprising:
a first wing and a second wing;
a hinge that forms a housing and that is attached to the first and the second wings, permitting the wings to rotate about the hinge when moving from a closed to an open position; and
a ratchet substantially within the housing that releasably holds the wings in the open position;
wherein the speculum, the wings, and the hinge each has a proximal end, a distal end, an exterior surface, and an interior surface;
wherein the wings and the hinge form a canopy that, when the wings are in the open position, creates and only partially surrounds an interior space that is not surrounded by any other portion of the compact speculum,
wherein the ratchet comprises a first ratchet component and a second ratchet component; and wherein the first ratchet component rotates together with the first wing, and the second ratchet component rotates together with the second wing,
wherein the first ratchet component is attached to the first wing,
wherein no portion of the compact speculum obstructs any portion of a length of the interior space opposite the hinge between the proximal end and the distal end of the compact speculum when the wings are in the open position, and
wherein the ratchet further comprises a ratchet engagement spring that releasably engages the first ratchet component with the second ratchet component.

4. The compact speculum of claim 3, further comprising a ratchet release button attached to the second ratchet component.

5. A compact speculum comprising:
a first wing and a second wing;
a hinge that forms a housing and that is attached to the first and the second wings, permitting the wings to rotate about the hinge when moving from a closed to an open position; and
a ratchet substantially within the housing that releasably holds the wings in the open position;
wherein the speculum, the wings, and the hinge each has a proximal end, a distal end, an exterior surface, and an interior surface;
wherein the wings and the hinge form a canopy that, when the wings are in the open position, creates and only partially surrounds an interior space that is not surrounded by any other portion of the compact speculum;
wherein no portion of the compact speculum obstructs any portion of a length of the interior space opposite the hinge between the proximal end and the distal end of the compact speculum when the wings are in the open position, and wherein:
the hinge comprises a pin and at least two hinge cylinders; and
the pin is hollow and houses the ratchet;
wherein at least one hinge cylinder pivots around the pin.

6. The compact speculum of claim 5, wherein each hinge cylinder is attached to one of the wings.

7. The compact speculum of claim 6, wherein the ratchet comprises a first ratchet component and a second ratchet component; and wherein the first ratchet component rotates together with the first wing and the second ratchet component rotates together with the second wing.

8. The compact speculum of claim 7, wherein the first ratchet component is attached to the first wing.

9. The compact speculum of claim 8, wherein the second ratchet component is attached to the pin, wherein the second ratchet component and the pin move together linearly along the hinge's axis of rotation to engage with or disengage from the first ratchet component.

10. The compact speculum of claim 9, wherein:
the pin comprises a key;
at least one of the hinge cylinders pivots around the pin, is attached to the second wing, and comprises a keyway;
the keyway is longer than the key; and
the key engages with the keyway to attach the pin and the second ratchet component to the second wing so as to lock rotation of the pin and the second ratchet component to the rotation of the second wing while allowing the linear motion of the pin and the second ratchet component.

11. A compact speculum comprising:
a first wing and a second wing;
a hinge that forms a housing and that is attached to the first and the second wings, permitting the wings to rotate about the hinge when moving from a closed to an open position; and
a ratchet substantially within the housing that releasably holds the wings in the open position;
wherein the speculum, the wings, and the hinge each has a proximal end, a distal end, an exterior surface, and an interior surface;
wherein the wings and the hinge form a canopy that, when the wings are in the open position, creates and only partially surrounds an interior space that is not surrounded by any other portion of the compact speculum;
wherein no portion of the compact speculum obstructs any portion of a length of the interior space opposite the hinge between the proximal end and the distal end of the compact speculum when the wings are in the open position, and wherein:
the hinge comprises a pin and one hinge cylinder;
the pin is hollow and substantially houses the ratchet; and
wherein the hinge cylinder pivots around the pin.

12. The compact speculum of claim 11, wherein the hinge cylinder is attached to one of the wings.

13. The compact speculum of claim 12, wherein the ratchet comprises a first ratchet component and a second ratchet component; and wherein the first ratchet component rotates together with the first wing and the second ratchet component rotates together with the second wing.

14. The compact speculum of claim 13, wherein the first ratchet component is attached to the first wing.

15. The compact speculum of claim 14, wherein the second ratchet component is attached to the pin, wherein the second ratchet component and the pin move together linearly along the hinge's axis of rotation to engage with or disengage from the first ratchet component.

16. The compact speculum of claim 15, wherein:
the pin comprises a key;
the hinge cylinder is attached to the second wing and the hinge cylinder comprises a keyway;
the keyway is longer than the key; and
the key engages with the keyway to attach the pin and the second ratchet component to the second wing so as to lock rotation of the pin and the second ratchet component to the rotation of the second wing while allowing the linear motion of the pin and the second ratchet component.

* * * * *